(12) United States Patent
Lenzi-Brangi et al.

(10) Patent No.: US 7,541,023 B2
(45) Date of Patent: Jun. 2, 2009

(54) HAIR BLEACH PRODUCT

(75) Inventors: Anne Marie Lenzi-Brangi, Orange, CT (US); Mary Larkin, South Salem, NY (US); Stephen Casperson, Milford, CT (US)

(73) Assignee: The Procter & Gamble Company, Cincinnati, OH (US)

( * ) Notice: Subject to any disclaimer, the term of this patent is extended or adjusted under 35 U.S.C. 154(b) by 641 days.

(21) Appl. No.: 10/392,682

(22) Filed: Mar. 20, 2003

(65) Prior Publication Data

US 2003/0206877 A1 Nov. 6, 2003

Related U.S. Application Data

(60) Provisional application No. 60/368,179, filed on Mar. 28, 2002.

(51) Int. Cl.
*A61Q 5/08* (2006.01)
(52) U.S. Cl. ......................... 424/62; 424/70.1
(58) Field of Classification Search .............. None
See application file for complete search history.

(56) References Cited

U.S. PATENT DOCUMENTS

| 4,226,852 | A | | 10/1980 | Tesmann et al. |
| 4,507,278 | A | | 3/1985 | DeMarco et al. |
| 5,294,436 | A | * | 3/1994 | Cope et al. ............... 424/62 |
| 6,703,004 | B2 | * | 3/2004 | Narasimhan et al. ....... 424/62 |
| 6,872,228 | B1 | * | 3/2005 | Lenzi-Brangi et al. ...... 8/110 |
| 6,919,073 | B2 | * | 7/2005 | Legrand et al. ............ 424/62 |
| 7,056,497 | B2 | * | 6/2006 | Lenzi-Brangi et al. ...... 424/62 |
| 2002/0139957 | A1 | | 10/2002 | Matsuo et al. |

FOREIGN PATENT DOCUMENTS

| JP | 62174005 | A2 | 7/1987 |
| JP | 02193911 | A2 | 7/1990 |
| JP | 02234971 | A2 | 9/1990 |
| JP | 09067235 | A2 | 3/1997 |
| JP | 09157142 | A2 | 6/1997 |
| JP | 2000256150 | A2 | 9/2000 |

* cited by examiner

*Primary Examiner*—Jyothsna A Venkat
(74) *Attorney, Agent, or Firm*—Melissa Krasovec; Marianne Dressman; Tara M. Rosnell

(57) ABSTRACT

The present invention relates to a hair bleach product containing a pigment or lake to provide a visual indication of where the bleach product was applied to the hair.

7 Claims, No Drawings

HAIR BLEACH PRODUCT

This patent application claims the benefit of U.S. Provisional Application No. 60/368,179 filed Mar. 28, 2002.

FIELD OF INVENTION

The present invention relates to hair bleach products. Specifically, the invention concerns hair bleach products that comprise in kit form a peroxide-based developer; a powder activator containing a persulfate oxidizing system, and an alkalizing agent, the hair bleach product further comprising a colorant selected from the group consisting of pigments, lakes, and mixtures thereof, the colorant indicating to the hair salon colorist or to the home user where on the hair the bleach product is being applied.

BACKGROUND OF THE INVENTION

Hair bleaching is a well known process in the hair cosmetic field. Hair bleaching involves the application of an oxidizing agent to the hair for a period of time effective to achieve a desired lighter hair shade. The oxidizing agent typically is a hydrogen peroxide solution in concentrations ranging from 6 to 12% by weight. The hydrogen peroxide is applied to the hair under alkaline pH conditions and gradually lightens the shade of the hair by oxidizing the melanin that gives it color. 28% Ammonium hydroxide is typically added to the peroxide solution at the time of use to provide the highly alkaline environment needed during use.

To enhance the lightening efficacy of the hydrogen peroxide oxidizer, it is known to incorporate a persulfate salt as a "booster". Sodium, potassium, ammonium persulfate salts, and mixtures thereof are provided in powder form, and are admixed with the hydrogen peroxide solution and the ammonium hydroxide solution at the time of use. The mixed product is then applied to the hair for a period of time effective to achieve the desired lighter hair shade. Because of the incorporation of the persulfate and when used with a 10 to 40% by volume hydrogen peroxide solution activated by the alkalizing agent, e.g., 28% ammonium hydroxide, substantial lightening of hair can be achieved. Such bleach products, typically sold in kit form, are provided to the industry as bleach blonding products and as hair bleach highlighting products.

A problem associated with such bleach products is that the colorist, that is, the individual applying the product to the hair, often a hair salon professional, but also the home user of such products, is unable to determine where the product has been applied to hair, or to gauge how much has been applied to the hair. This is because the product as applied to the hair, i.e., the mixture of the developer, the powder activator and the alkalizing agent, is somewhat transparent or translucent, and is not adequately visible when present on the hair. This problem is exacerbated where the hair to be bleached has multiple shades or highlights occasioned by prior hair coloring treatments.

Accordingly, it is an object of the present invention to provide a hair bleach product that can be visibly applied to the hair.

It is a preferred object of the invention to provide a hair bleach product containing a colorant selected from the group consisting of water insoluble pigments, lakes and mixtures thereof.

It is another object of the invention to provide a hair bleach product in kit form comprising an alkalizing agent composition, a hydrogen peroxide developer composition and a persulfate activator powder composition containing a colorant selected from the group consisting of water insoluble pigments, lakes and mixtures thereof.

SUMMARY OF THE INVENTION

The hair bleach product of the present invention is in kit form and comprises in separate packages within the kit a peroxide developer; a powder activator, and an alkalizing agent composition.

The peroxide developer contains from about 6 to about 12% by weight hydrogen peroxide (corresponding to a 20 to 40 volume solution), which is an oxidizing agent capable of lightening hair to some extent.

The powder activator contains from about 40 to about 80% by weight of an alkali metal persulfate selected from the group consisting of sodium persulfate, potassium persulfate, and ammonium persulfate.

The alkalizing agent component composition preferably has a thickened liquid, gel, cream or other substantially non-flowing rheology and contains from about 10 to about 25% by weight of an alkalizing agent selected from the group consisting of ammonium hydroxide and monoethanolamine.

At least one of the component compositions in the hair bleach product, or a separate component of the kit, contains a colorant for use, when the hair bleach product is applied to the hair, as a visual cue to the colorist to indicate where the product is being applied to the hair. The colorant is selected from the group consisting of water insoluble pigments, lakes and mixtures thereof. Preferably, the colorant is present in the powder activator component. In any event, the colorant should be compatible with the other components of the hair bleach product, and in particular compatible with the persulfate, the alkalizer, and especially the oxidizing agent, usually hydrogen peroxide.

DETAILED DESCRIPTION OF THE INVENTION

The hair bleach product is adapted to provide sufficient lightening within a given period of time so that hair may be bleached to a blonde shade. The hair bleach product of the present invention comprises (a) a peroxide solution, generally referred to in the field as the developer component; (b) a powder activator component, also referred to in the field as a lightening powder or a booster, and (c) an alkalizing agent component.

These three components (a), (b) and (c) are typically provided in the form of a kit, which further includes instructions for use, and which optionally may contain a hair pretreatment component or a hair post treatment component. The three essential components (a), (b) and (c) of the hair bleach product kit are admixed at the time of use in an applicator device that is preferably part of the kit, typically a container for one of the three components (a), (b) or (c).

At least one of the component compositions in the hair bleach product, or a separate component of the kit, contains a colorant for use, when the hair bleach product is applied to the hair, as a visual cue to the colorist to indicate where the product is being applied to the hair. The colorant is selected from the group consisting of water insoluble pigments, lakes and mixtures thereof. Preferably, the colorant is present in the powder activator component. In any event, the colorant should be compatible with the other components of the hair bleach product, and in particular compatible with the persulfate, the alkalizer, and especially the oxidizing agent, usually hydrogen peroxide.

The Developer Component

The developer component composition comprises a hydrogen peroxide solution. The solution contains from about 6 to about 12% by weight hydrogen peroxide. (This corresponds to a 20 to 40 volume solution, and is referred to as, e.g., 20 volume, 30 volume or 40 volume hydrogen peroxide. This concentration unit refers to the amount of oxygen released from one volume of the hydrogen perioxide solution. Thus, one volume of a 30 volume peroxide solution is able to liberate 30 volumes of oxygen.)

The developer component composition preferably contains additional ingredients to facilitate its use and performance. Thus, the developer component composition further contains one or more of the following adjuvants: a thickener, an emulsifier, or a hair conditioning agent. Each of these constituents is present in the developer component in sufficient amount to provide its intended function in the developer component composition or in the final product mixture when the developer component is mixed with the activator powder component and the alkalizing agent component. Suitable adjuvants are those that are stable to hydrogen peroxide. Suitable thickeners are, for example, cetearyl alcohol and stearamidopropyl dimethylamine. Nonionic polymeric thickeners, in particular polyether urethanes sold under the tradename Aculyn by Rohm & Haas Company, especially Aculyn 44 and 46, are suitable. Anionic acrylate polymers, e.g., such polymers sold under the tradename Aculyn, e.g., Aculyn 22, 28 and 33, by Rohm and Haas may be used. Other useful thickeners are identified in International Cosmetic Ingredient Dictionary and Handbook, v.2, pages 1810-1812 ($8^{th}$ Edition 2000) (CFTA) incorporated by reference herein, although stability in the presence of hydrogen peroxide would have to be confirmed with the manufacturers. Generally, the thickening agents are present in an amount effective to provide a viscosity of from 3,000 to about 40,000 cps, preferably 5,000 to about 30,000 cps, measured at 25° C. and atmospheric pressure, as measured using a Brookfield VLT viscometer with appropriate spindle type and a suitable speed setting, e.g., No. 3 spindle at 6 rpm for 60 seconds. Typically, the thickener is present in an amount ranging from about 0.05% to about 5%, preferably about 0.1 to about 2.5%, depending on the choice of thickener agent and the degree of thickening that is desired.

The emulsifiers present in the developer component are typically in the range of from about 0.05 to about 10% preferably from about 0.1 to about 5%, especially 0.5 to 2.5% by weight of the developer composition. Suitable emulsifiers are glyceryl stearate, oleth 2, oleth-10, PEG-75 lanolin and ceteareth-20. Often, mixtures of emulsifiers are employed. The emulsifiers, which are surface active agents, may also contribute to thickening of the composition. Other emulsifiers are identified in the above-cited CTFA Ingredient Dictionary and Handbook, v.2, at pages 1795-1803. Compatability with peroxide should be confirmed.

The developer composition may further contain an antifoam material such as simethicone in low concentration, to prevent foaming during manufacture, an acidifying material, a preservative, etc. while conventional hair conditioning agents may be incorporated in the developer if compatible at the acidic conditions and in the presence of hydrogen peroxide. Conditioning agents are generally incorporated in the alkalizer component.

The pH of the developer component is generally in the range of from about 2.5 to about 5.5, especially about 3.0 to about 4.

Generally, the colorant as previously described is not contained in the developer component. Because the colorant is insoluble, it would have to be suspended in the developer component composition, which adds additional complexity during manufacture, as well as difficulties occasioned by precipitation during storage.

The Powder Activator Component

The powder activator component of the present invention comprises an alkali metal persulfate selected from the group consisting of sodium persulfate, potassium persulfate, ammonium persulfate, and mixtures thereof. The powder activator component contains from about 40 to about 80%, preferably 50 to 70%, of the persulfate by weight of the activator component composition. The preferred alkali metal persulfate is a mixture of ammonium persulfate and potassium persulfate. Sodium persulfate may also be used.

The powder activator component further contains an alkalinity agent to ensure an alkaline bleach product when the product components are mixed. Suitably, the alkalinity agent is sodium silicate present in the activation powder component in an amount of from about 20 to about 50% by weight of the powder activator component composition, preferably from about 30 to 40% by weight.

Preferably, the colorant selected from the group consisting of water insoluble pigments or lakes and mixtures thereof (hereinafter "pigment") is present in the powder activator component, generally in an amount of up to about 2.5% by weight of the powder activator component, preferably from about 0.1 to about 2% by weight. The pigment should be compatible with the other ingredients in the hair bleach product, and in particular it should be compatible with hydrogen peroxide. The pigment imparts to the hair bleach product a color that is visible when the product is applied to the hair, and thus imparts a visual cue to the hair colorist as to where the product is being applied. Suitable pigments include ultramarine blue, D&C Yellow No. 10 aluminum lake, chromium oxide green, titanium dioxide, D&C Red No. 30 lake, and D&C Yellow No. 5 zirconium lake.

A dessicant such as silica is also typically incorporated to prevent moisture from prematurely reacting with the presulfates. The silica is a positive amount generally less than about 5% by weight, usually from about 0.1% to about 3% by weight of the activator component. A lubricant may be incorporated to assist in dry blending of the powder materials, for example, a surfactant such as sodium lauryl sulfate may be incorporated in an amount of up to about 3% by weight of the composition. Each of the adjuvant constituents is present in the powder activator component in sufficient amount to provide its intended function in the powder activator component composition or in the final product mixture when mixed with the developer and the alkalizing agent.

The Alkalizing Agent Component

The third essential component is the alkalizing agent component. The alkalizing agent in the alkalizing agent component is selected from the group consisting of ammonium hydroxide, monoethanolamine, and mixtures thereof.

This component composition generally has a pH of from about 10 to 12, preferably from about 10.5 to 11.5, especially about 11, by incorporating an effective amount of the alkalizing agent to achieve such pH values. Generally, the alkalizing agent is present in an amount of from about 3 to about 25% by weight of the alkalizing agent component, depending upon the alkalizing agent used. For monoethanolamine, the concentration is about 10 to 25% preferably about 12 to about 21% by weight. Where ammonium hydroxide is the alkalizing agent, its concentration in the alkalizer agent component is from about 3 to about 15% by weight, measured as a 28% by weight ammonium hydroxide solution, preferably from about 5 to about 12%. In any event the alkalizing agent is present in an amount effective to obtain the requisite pH set forth above.

Preferably, the alkalizing agent component is in the form of a thickened liquid, a gel or a cream, which form facilitates its admixture with the developer and activator powder components, although aqueous solutions, e.g., thin lotions, can be used.

The adjuvants useful in achieving the desired form of the alkalizing agent component and their incorporation to form the gel, the cream or the thickened liquid are well known to those of ordinary skill in the art. Such useful adjuvants are thickeners, surface active agents, and emulsifiers, all as described above in the section on the developer component. Also useful as adjuvants are fragrances, dyes, herbal extracts, and the like.

A gel composition is obtainable using oleic acid as a gelling agent and may further include a blend of anionic and nonionic surface active agents. Suitably, the oleic acid gelling agent is present in an amount of from about 0.1 to about 10% by weight of the alkalizing agent component. The surface active agents are typically present in an amount of from about 0.1 to about 15% by weight.

A cream composition having a viscosity of from about 50,000 to about 700,000 cps, preferably from about 100,000 to about 500,000 cps at 25° C. and atmospheric pressure, as measured using a Brookfield VLT viscometer at requisite parameters, i.e., a T-D spindle at 6 rpm descending for 60 seconds, can be obtained with a suitable amount of a surfactant thickening system. Useful surfactants are stearamide MEA, cocamide MEA, cetyl alcohol, myristyl alcohol, cetearyl alcohol, behenamidopropyl betaine, and stearamidopropyl betaine. Other thickening agents include the previously mentioned polyether urethane and polyacrylic acid-based polymers.

Conditioning agents may also be incorporated in amounts of from 0.1 to about 10%, preferably 0.5 to 5% by weight of the alkalizing component composition. Suitable conditioners are identified in the CTFA Ingredient Dictionary and Handbook referred to above at v.2, pages 1752-1759 incorporated by reference, in particular betaines, such as cocamideopropyl betaine, and linoleamido propyl dimethyl amine dimer dilinoleate. Also useful is Polyquaternium 47, sold as Merquat 2001 by Nalco, Inc.

Generally, the pigment as previously described is not contained in the alkalizing agent component. Because the pigment is insoluble, it would have to be suspended in this component composition, which adds additional complexity during manufacture, as well as difficulties occasioned by precipitation during storage.

The Kit

The kit comprises premeasured amounts of the developer component, the powder activator component and the alkalizing agent component, along with instructions for use, an applicator tip for connection to the developer container, and gloves.

The developer component is preferably provided in a container which also serves as the container for mixing the components, and, with applicator tip installed, is used to apply the bleach product to the hair. The developer component container has sufficient head space to allow for the mixing of the other components.

The activator powder component is contained in a foil pouch packet, the entire contents of which are emptied by the consumer into the developer component container.

Lastly, the alkalizing agent component, which preferably is in gel form and contained in a tube, is added to the developer container applicator container.

The hair bleach product composition applied to the hair (i.e., the mixture of the three components) has a viscosity of from about 20,000 to about 60,000 cps, preferably from about 30,000 to about 45,000 cps at 25° C. and atmospheric pressure, as measured using a Brookfield VLT viscometer at requisite parameters, i.e., a T-D spindle at 6 rpm descending for 60 seconds. The product remains on the hair until the desired lightening of the hair is achieved. Generally, this period of time is less than about 45 minutes.

The proportions of the three components used in the process are adapted so that there is no excess product or residual components of the product remaining after use. The proportions are predetermined so that the proper consistency of the product and the desired concentrations of the active ingredients as well as the adjuvants separately contained in one or more of the product component compositions are achieved on admixture of the three components, and so that the final product pH will be from about 10 to about 12, preferably from about 10.5 to about 11.5, especially about 11.

The final bleach product composition, based on mixing of the three essential component compositions comprises on an active ingredient basis:

|  | Range wt./o | Preferred Concentration (wt./o) |
| --- | --- | --- |
| Hydrogen Peroxide | about 3-about 7.5 | 4-6 |
| Alkali Metal Persulfate | about 3-about 12 | 5-9 |
| Alkalizing Agent | about 2.5-about 7.5 | 4-6 |
| Pigment | about 0.1-about 2.5 | 1-2 |

The kit typically comprises from about 60 to about 220 ml. developer component; from about 14 to about 56 g. powder activator component; and from about 28 to about 112 g. alkalizing agent component. The kit generally comprises from about 3 to 5 parts developer component per part of activator powder component and from about 1.5 to about 2.5 parts alkalizing agent component per part of activator powder component. In a preferred embodiment 4 parts developer (112 g.), 1 part powder activator (28 g.) and 2 parts alkalizing agent component (56 g.) are mixed to provide the bleach composition applied to the hair. In this embodiment the developer contains about 30 volume hydrogen peroxide (about 9% by weight); the powder activator contains about 60% by weight of persulfates, and the alkalizing agent component contains about 18% by weight alkalizing agent.

Use of the Bleach Product

As described above the powder activator composition is added from its packet into the developer component, preferably in the applicator container, followed by addition of the alkalizing agent component. The contents are then mixed by shaking. Using the applicator tip, the final hair bleach product composition is applied to the hair. Because of the color imparted to the bleach product by the pigment, the hair colorist or to the consumer receives a visual indication where the product has been applied on the hair. This is particularly important when substantially the entire head of hair of the consumer is to be bleached with the same bleach product composition, i.e., where the salon colorist or in home consumer does not use a cap or foil that isolates discrete small portions of hair for application of a bleach product, as in highlighting and streaking techniques. The degree of lightening is checked periodically, and when the desired level of lightening is obtained, most usually in less than 45 minutes even for black hair, the product is rinsed from the hair, and the hair is preferably shampooed. Following rinsing a hair conditioner, which may also be included in the kit, can be applied to the hair.

Product Manufacture

The hair bleach product of the present invention is made by conventional processes known in the art for making hair bleach products, and comprises admixing the ingredients of each of the component compositions in suitable vessels, followed by packaging in appropriate individual containers.

The present invention is further illustrated by the examples that follow. Unless otherwise indicated all percentages referred to herein are percent by weight on an active ingredient basis of the component compositions or of the mixed bleach product composition, as the case may be.

EXAMPLES

The composition of Examples 1 through 4 are prepared. Each product on a weight basis comprises 4 parts of the developer component, 1 part of the powder activator component, and 2 parts of the alkalizing agent component.

The hair bleach product of each Example 1 to 4 is applied to the hair of a consumer, the pigment permitting uniform distribution of the product throughout the hair, all areas of the hair receiving an essentially equal amount of bleach product. After 45 minutes the product is shampooed from the hair, which have blonde colorations.

| Components | Example 1 Weight % | Example 2 Weight % | Example 3 Weight % | Example 4 Weight % |
|---|---|---|---|---|
| Developer Component | | | | |
| Hydrogen Peroxide (50% active) | 18.3 | 18.3 | 18.3 | 18.3 |
| Water | 73.85 | 73.85 | 73.85 | 73.849 |
| Glyceryl Stearate | 3.63 | 3.63 | 3.63 | 3.63 |
| Cetearyl Alcohol | 0.965 | 0.965 | 0.965 | 0.965 |
| Ceteareth-20 | 0.322 | 0.322 | 0.322 | 0.322 |
| PEG-75 Lanolin (50% wt active) | 0.74 | 0.74 | 0.74 | 0.74 |
| Wax | 0.73 | 0.73 | 0.73 | 0.73 |
| Stearamidopropyl Dimethylamine | 0.6 | 0.6 | 0.6 | 0.6 |
| Etidronic Acid (60% wt active) | 0.27 | 0.27 | 0.27 | 0.27 |
| Oleth-10 | 0.25 | 0.25 | 0.25 | 0.25 |
| Oleth-2 | 0.25 | 0.25 | 0.25 | 0.25 |
| Simethicone | 0.1 | 0.1 | 0.1 | 0.1 |
| | 100.0 | 100.0 | 100.0 | 100.0 |
| Activator Powder Component | | | | |
| Potassium Persulfate (98.4% wt active) | 56 | 60 | 39 | 60 |
| Sodium Persulfate (98.4% wt active) | 3 | | | |
| Ammonium persulfate (98% wt active) | | | 19 | 20 |
| Silica | 2.7 | 2.7 | 2.75 | 1.6 |
| Sodium Lauryl Sulfate | 1 | 1 | 1 | 1.2 |
| Ultramarine Blue | 1 | 0.5 | 1.5 | 2 |
| Disodium EDTA | 1 | 1 | 1 | 1.2 |
| Sodium Silicate | 35.3 | 34.8 | 35.75 | 14 |
| | 100.0 | 100.0 | 100.0 | 100.0 |
| Alkalizing Agent Component | | | | |
| Water | Q.S. | Q.S. | Q.S. | Q.S. |
| Ethanolamine | 6 | | | 18 |
| Soytrimonium Chloride | 5.85 | 5.85 | 5.85 | 5.85 |
| Propylene Glycol | 12.375 | 13.875 | 13.875 | 13.875 |
| Steareth-21 | 2 | 2 | 2 | 2 |
| Oleamide MIPA | 1 | 1 | 1 | 1 |
| Erythorbic Acid | 0.4 | 0.4 | 0.4 | 0.4 |
| Sodium sulfite | 0.1 | 0.1 | 0.1 | 0.1 |
| EDTA | 0.2 | 0.2 | 0.2 | 0.2 |
| C12-15 Pareth-3 | 5.4 | 5.4 | 5.4 | 5.4 |
| C11-15 Pareth-9 (90 % wt active) | 0.7 | 0.7 | 0.7 | 0.7 |
| Oleic Acid | 4.365 | 4.365 | 4.365 | 4.365 |
| Ammonium Hydroxide (28% wt active) | 12 | 8 | 15 | |
| Botanical Extracts | 0.14 | 0.14 | 0.14 | 0.14 |
| Fragrance | 1.475 | 1.575 | 1.575 | 1.575 |
| Ethoxydiglycol | 2.915 | 2.915 | 2.915 | 2.915 |
| Cocamidopropyl Betaine (30% active) | 2.915 | 2.915 | 2.915 | 2.915 |
| PEG-150/Stearyl/SMDI Copolymer | 2.665 | 2.665 | 2.665 | 2.665 |
| (19% wt active) | | | | |
| | 100 | 100 | 100 | 100 |

What is claimed is:

1. A hair bleach product in kit form comprising:
   (a) a peroxide-based developer component containing from about 6 to about 12% hydrogen peroxide by weight of the developer component;
   (b) a powder activator component comprising from about 40 to about 80% by weight of the activator powder component of an alkali metal persulfate selected from the group consisting of sodium persulfate, potassium persulfate, and ammonium persulfate,
   (c) an alkalizing agent component comprising in an aqueous vehicle from about 3 to about 25% of an alkalizing agent by weight of the alkalizing agent component, and
   (d) a colorant is contained in the powder activator component (b) and the colorant is present in an amount of from about 0.1 to about 2.5% by weight of the powder activator component, wherein the colorant selected from the group consisting of ultramarine blue, D&C Yellow No. 10, aluminum lake, D&C Red No.30 lake, and D&C Yellow No.5 zirconium lake to provide a visual indication to the hair colorist upon application of the hair bleach product to the hair
   wherein the product, upon admixture of components (a), (b), (c), and (d) and as it is applied to the hair, contains, on a weight basis, from about 4 to 6% hydrogen peroxide, from about 5 to 9% alkali metal persulfate from 4 to 6% alkalizing agent and from 1 to 2% colorant.

2. The hair bleach product of claim 1 wherein the developer component contains about 9% hydrogen peroxide.

3. The hair bleach product of claim 1 wherein the alkalizing agent component is selected from the group consisting of ammonium hydroxide and monoethanolamine.

4. The hair bleach product of claim 3 wherein the alkalizing agent component is ammonium hydroxide present in an amount of from about 3 to about 15% measured as a 28% solution.

5. The product of claim 1 wherein the product as applied to the hair has a viscosity of from about 20,000 to 60,000 cps.

6. A method of bleaching hair comprising mixing components (a), (b), (c) and (d) of the hair bleach product of claim 1; applying the resulting mixture to hair for a period at time effective to lighten the hair, and removing the resulting mixture from the hair.

7. The method of claim 6 wherein the product as applied to the hair has a viscosity of from about 20,000 to 60,000 cps.

* * * * *